US010088445B2

(12) United States Patent
Nakamura

(10) Patent No.: US 10,088,445 B2
(45) Date of Patent: Oct. 2, 2018

(54) GAS SENSOR

(71) Applicant: DENSO CORPORATION, Kariya, Aichi-pref. (JP)

(72) Inventor: Masatake Nakamura, Kariya (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 15/539,300

(22) PCT Filed: Dec. 11, 2015

(86) PCT No.: PCT/JP2015/084755
§ 371 (c)(1),
(2) Date: Jun. 23, 2017

(87) PCT Pub. No.: WO2016/104176
PCT Pub. Date: Jun. 30, 2016

(65) Prior Publication Data
US 2017/0356874 A1 Dec. 14, 2017

(30) Foreign Application Priority Data
Dec. 25, 2014 (JP) .................. 2014-263012

(51) Int. Cl.
*G01N 27/407* (2006.01)
*G01N 27/406* (2006.01)
*G01N 27/409* (2006.01)

(52) U.S. Cl.
CPC ....... *G01N 27/4078* (2013.01); *G01N 27/409* (2013.01)

(58) Field of Classification Search
CPC .. G01N 27/406; G01N 27/407; G01N 27/416; G01N 27/409; G01N 27/4077
See application file for complete search history.

(56) References Cited

U.S. PATENT DOCUMENTS 4,019,974 A * 4/1977 Weyl .................. G01N 27/4062
204/428
5,829,306 A 11/1998 Komazaki et al.
(Continued)

FOREIGN PATENT DOCUMENTS

JP   2012-141286        7/2012
JP   2012141286 A  *   7/2012

OTHER PUBLICATIONS

International Search Report dated Feb. 16, 2016 issued in PCT/JP2015/084755 (2 pgs.).

*Primary Examiner* — Susan D Leong
(74) *Attorney, Agent, or Firm* — Nixon & Vanderhye P.C.

(57) ABSTRACT

A gas sensor includes a sensor device, a device-side insulator porcelain, an atmospheric side insulator porcelain, a housing, a seal disposed between the housing and the device-side insulator porcelain, and an atmospheric side cover. The atmospheric side cover includes a large-diameter portion, a small-diameter portion, and a shoulder portion formed therebetween. The shoulder portion presses a base end surface of the atmospheric side insulator porcelain to a front end side through a biasing member to place the atmospheric side insulator porcelain in contact with the device-side insulator porcelain. The shoulder portion is defined by a contact portion placed in contact with the biasing member and a detached portion separate from the biasing member to form a communication path which communicates between an outer space and an outside path. This avoids entry of measurement gas into an air atmosphere within the atmospheric side insulator porcelain to obtain correct sensor outputs, also avoids breakage of the atmospheric side insulator porcelain, and reduces the manufacturing costs.

4 Claims, 11 Drawing Sheets

(56) References Cited

U.S. PATENT DOCUMENTS

| | | |
|---|---|---|
| 2002/0017128 A1 | 2/2002 | Shirai |
| 2004/0124082 A1* | 7/2004 | Nakagawa ......... G01N 27/4077 204/424 |
| 2004/0129566 A1* | 7/2004 | Nakagawa ......... G01N 27/4077 204/424 |
| 2005/0138989 A1 | 6/2005 | Noda et al. |
| 2007/0175267 A1 | 8/2007 | Yamauchi et al. |
| 2007/0175754 A1 | 8/2007 | Toguchi et al. |
| 2007/0220955 A1 | 9/2007 | Noda et al. |
| 2013/0305811 A1 | 11/2013 | Noda et al. |

* cited by examiner

GAS SENSOR

This application is the U.S. national phase of International Application No. PCT/JP2015/084755 filed Dec. 11, 2015 which designated the U.S. and claims priority to JP Patent Application No. 2014-263012 filed Dec. 25, 2014, the entire contents of each of which are hereby incorporated by reference.

TECHNICAL FIELD

The present invention generally relates to a gas sensor.

BACKGROUND ART

Gas sensors are known which are installed in an exhaust system of an internal combustion engine such as an automotive engine to detect a specified gas such as an oxygen concentration in exhaust gas (i.e., measurement gas). For instance, Japanese Patent First Publication No. 2007-199005 discloses a gas sensor which includes a sensor device which measures the concentration of a given gas component in the measurement gas, a device-side insulator porcelain which retains the sensor device therein, an atmospheric side insulator porcelain which covers a base end side of the sensor device to form an air atmosphere, a housing which retains the insulator porcelains therein, and an atmospheric side cover secured to a base end side of the housing. The atmospheric side cover includes a large-diameter portion on a front end side, a small-diameter portion on a base end side, and a shoulder between the large-diameter portion and the small-diameter portion. The shoulder presses a base end surface of the atmospheric side insulator porcelain through a biasing member to a front end side to place the atmospheric side insulator porcelain in contact with the device-side insulator porcelain. A seal made of a compressed sealing member such as talc is disposed between the housing and the device-side insulator porcelain to isolate between an air atmosphere formed as a reference gas inside the atmospheric side insulator porcelain and a measurement gas atmosphere in which the measurement gas exists.

SUMMARY OF THE INVENTION

Problem to be Solved by the Invention

The above described gas sensor is installed in an internal combustion engine, so that the compressed sealing member may be exposed to high temperatures and high pressures for a long period of time, thereby resulting in deformation thereof. Such deformation results in formation of an air gap between the sealing member and the device-side insulator porcelain, thus causing the measurement gas to enter inside the atmospheric side cover and flow into the air atmosphere within the atmospheric side insulator porcelain, which may lead to a change in concentration of oxygen in the air atmosphere as the reference gas. This results in a difficulty in obtaining correct sensor outputs. In view of such a problem, various proposals of how to select materials of the sealing member or compress the sealing member have been made in order to decrease the deformation of the sealing member arising from the high temperature or the high pressure. It is, however, impossible for either approach to completely avoid the deformation of the sealing member. There is, therefore, room for improvement in obtaining correct sensor outputs.

In order to achieve the correct sensor outputs, the atmospheric side insulator porcelain may be pressed against the device-side insulator porcelain to achieve close adhesion therebetween to prevent gas, as escaping from the seal, from passing between the atmospheric side insulator porcelain and the device-side insulator porcelain and flowing into the air atmosphere and selectively direct a flow of the gas outside the atmospheric side insulator porcelain. In such a structure, however, space outside the atmospheric side insulator porcelain is enclosed by the atmospheric side cover and the biasing member, so that the gas is accumulated in that space. When the gas continues to be accumulated in the space, it will lead to a risk that the gas finally passes between the atmospheric side insulator porcelain and the device-side insulator porcelain and then flows into the air atmosphere within the atmospheric side insulator porcelain.

In order to prevent the leaking gas from continuing to be accumulated in the space outside the atmospheric side insulator porcelain in the above structure, the base end surface of the atmospheric side insulator porcelain may be shaped to have irregularities to define clearances between the base end surface and the atmospheric side cover to form gas drain paths leading to air holes of the atmospheric side cover. In such a structure, however, load which presses the atmospheric side insulator porcelain against the device-side insulator porcelain is exerted on the irregularities on the atmospheric side insulator porcelain, so that stress will partially concentrate on the irregularities, which may result in breakage of the atmospheric side insulator porcelain. The formation of the irregularities on the base end surface of the atmospheric side insulator porcelain will also result in a complicated configuration of the atmospheric side insulator porcelain, thus leading to an increase in manufacturing cost.

The present invention was made in view of the above background. It is an object to provide a gas sensor which is designed to avoid entry of measurement gas into an air atmosphere within an atmospheric side insulator porcelain to obtain correct sensor outputs, also avoid breakage of the atmospheric side insulator porcelain, and reduce manufacturing costs.

Means for Solving the Problem

One aspect of the invention is a gas sensor comprising: a sensor device which detects a concentration of a given gas component of measurement gas; a device-side insulator porcelain which retains the sensor device therein; an atmospheric side insulator porcelain which covers a base end side of said sensor device to define an air atmosphere; a housing which retains said the device-side insulator porcelain and said atmospheric side insulator porcelain therein; a seal which is made of a sealing member disposed between an inner peripheral surface of the housing and an outer peripheral surface of the device-side insulator porcelain; and an atmospheric side cover which is secured to a base end side of said housing.

The atmospheric side cover includes a large-diameter portion which is formed on a front end side thereof, a small-diameter portion which is formed closer to the base end side than the large-diameter portion is and has a diameter smaller than that of the large-diameter portion, a shoulder portion which is formed between the small-diameter portion and the large-diameter portion to press a base end surface of the atmospheric side insulator porcelain to the front end side through a biasing member to place the atmospheric side insulator porcelain in contact with the device-side insulator porcelain, and an air hole which is formed in a base end portion.

An outer space is formed between an outer peripheral surface of the atmospheric side insulator porcelain and an inner peripheral surface of the large-diameter portion. The outer space is arranged adjacent to the seal.

An outside path is formed inside the small-diameter portion in communication with the air hole.

The shoulder portion includes a contact portion which contacts the biasing member and a detached portion which is separate from the biasing member. A communication path is formed between the detached portion and the biasing member to establish communication between the outer space and the outside path.

Effect of the Invention

According to the above gas sensor, the measurement gas leaking from the seal reaches the outer space formed adjacent the seal. The measurement gas flows in the outside path through the communication path formed in the shoulder portion and then is discharged from the air hole outside the atmospheric side cover. The shoulder portion of the atmospheric side cover presses the atmospheric side insulator porcelain against the device-side insulator porcelain through the biasing member, thereby achieving close adhesion therebetween to create an air-tight seal. This avoids the entry of the measurement gas into the air atmosphere formed as a reference gas within the atmospheric side cover, thereby obtaining correct sensor outputs. The detached portion and the contact portion which define the communication path are provided by the shoulder portion of the atmospheric side cover, thereby alleviating concentration of stress on the base end surface of the atmospheric side insulator porcelain as compared with when the base end surface of the atmospheric side insulator porcelain is shaped to have irregularities, which avoids the breakage of the atmospheric side insulator porcelain. The detached portion and the contact portions of the shoulder portion of the atmospheric side cover may be made easily using a press, thus resulting in a decrease in manufacturing cost as compared with when the base end surface of the atmospheric side insulator porcelain is shaped to have irregularities to define a path between itself and the shoulder portion of the atmospheric side cover.

The communication path is formed on the shoulder portion of the atmospheric side cover, so that it is located closer to the external atmosphere, thereby facilitating dissipation of heat therefrom, so that it is kept at a relatively low temperature as compared with when the atmospheric side insulator porcelain is shaped to have irregularities to define a flow path between itself and the outer shoulder portion. Such thermophoresis causes the measurement gas leaking from the seal to actively flow in the communication path that is lower in temperature, not inside the atmospheric side insulator porcelain that is higher in temperature, thereby avoiding the entry of the measurement gas escaping from the seal into the air atmosphere in the atmospheric side insulator porcelain to ensure more correct sensor outputs.

As apparent from the above discussion, this invention provides a gas sensor which is designed to avoid the entry of the measurement gas into the air atmosphere within the atmospheric side insulator porcelain, thereby obtaining correct sensor outputs, eliminating a risk of breakage of the atmospheric side insulator porcelain, and decreasing the manufacturing costs thereof.

EMBODIMENT FOR CARRYING OUT THE INVENTION

The above described gas sensor may be used in A/F sensors, $O_2$ sensors, NOx sensors, or PM sensors.

In this disclosure, a side which is disposed in an exhaust pipe of an internal combustion engine for automobiles will be referred to as a front end side, and the opposite side will be referred to a base end side. A lengthwise direction of a sensor device will be referred to as an axial direction.

EMBODIMENT

Embodiment 1

Figure 1:
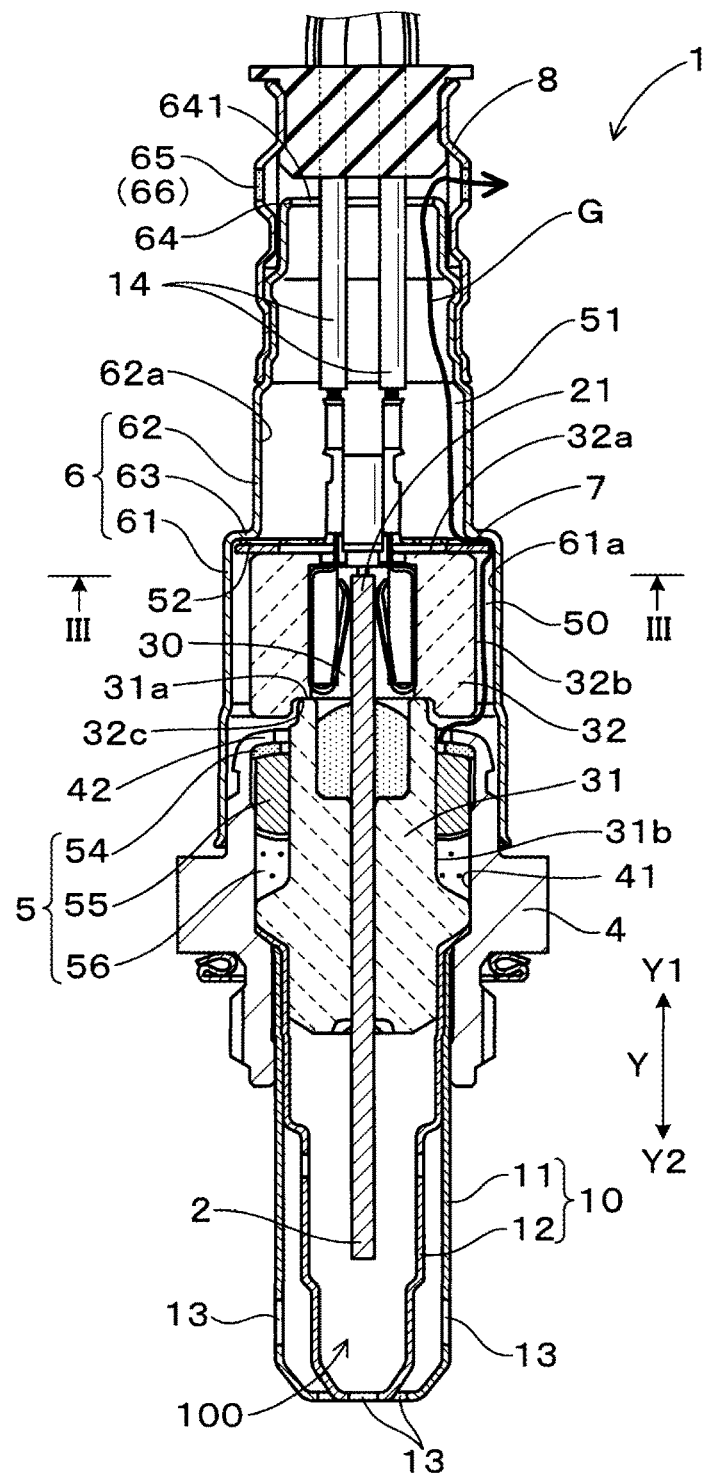
FIG. 1 is a sectional view of a gas sensor in an embodiment 1.

The gas sensor 1 of this embodiment will be described using FIGS. 1 to 7. The gas sensor 1, as illustrated in FIG. 1, includes the sensor device 2, the device-side insulator porcelain 31, the atmospheric side insulator porcelain 32, the housing 4, the seal 5, and the atmospheric side cover 6. The sensor device 2 works to measure the concentration of a given gas component of a measurement gas. The device-side insulator porcelain 31 has the sensor device 2 retained therein. The atmospheric side insulator porcelain 32 covers the base end side 21 of the sensor device 2 and define the air atmosphere 30 therein. The housing 4 has the device-side insulator porcelain 31 and the atmospheric side insulator porcelain 32 retained therein. The seal 5 is made of the sealing member 56 disposed between the inner peripheral surface 41 of the housing 4 and the outer peripheral surface 31b of the device-side insulator porcelain 31. The atmospheric side cover 6 is secured on the base end side Y1 of the housing 4.

The atmospheric side cover 6 includes the large-diameter portion 61 which is formed on the front end side Y2, the small-diameter portion 62 which is formed to be closer to the base end side Y1 than the large-diameter portion 61 is and has a diameter smaller than that of the large-diameter portion 61, the outer shoulder portion 63 which is formed between the small-diameter portion 62 and the large-diameter portion 61 and presses the base end surface 32a of the atmospheric side insulator porcelain 32 to the front end side Y2 through a biasing member (the disc spring 7), and the air hole 641 formed in the base end portion 64. The outer space 50 is formed adjacent the seal 5 between the outer peripheral surface 32b of the atmospheric side insulator porcelain 32 and the inner peripheral surface 61a of the large-diameter portion 61. The outside path 51 is formed in the small-diameter portion 62 in communication with the air hole 641. The outer shoulder portion 63 includes the contact portions 631 which are placed in contact with the biasing member (i.e., the disc spring 7) and the detached portions 632 (which will also be referred to as a non-contact portion) which is separate from the biasing member (i.e., the disc spring 7). The communication path 52 which communicates between the outer space 50 and the outside path 51 is formed between the detached portions 632 and the biasing member (i.e., the disc spring 7).

The gas sensor 1 will be described below in detail.

The gas sensor 1 is attached to an exhaust pipe through the housing 4 with the atmospheric side cover 6 located outside the exhaust pipe.

Figure 2:
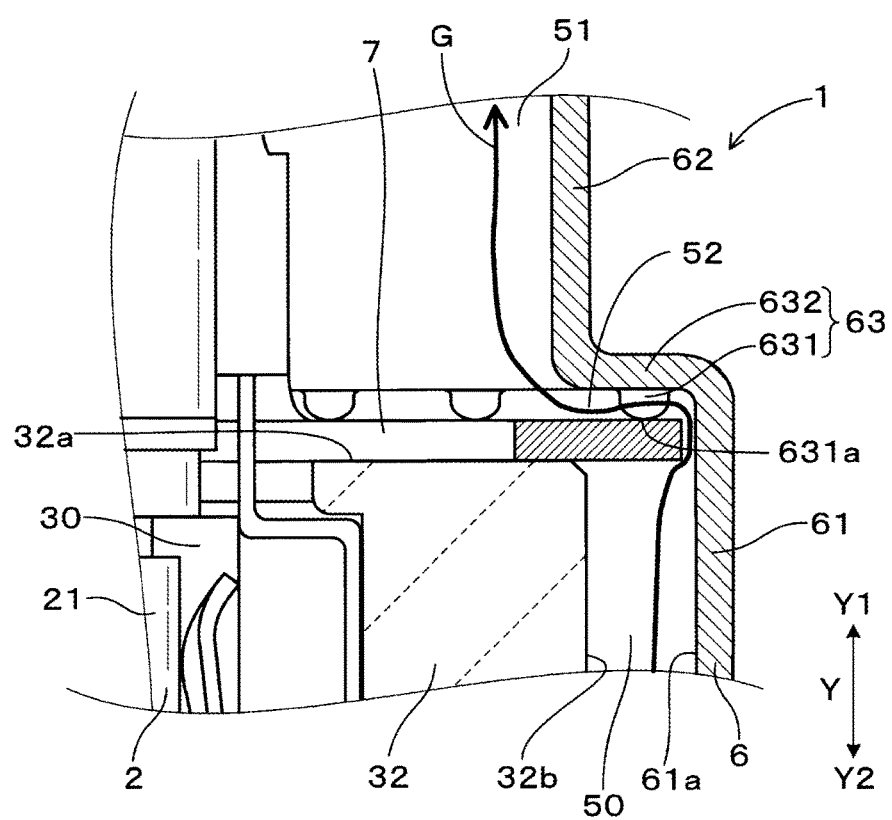
FIG. 2 is an enlarged view around a region of a shoulder portion in FIG. 1.
Figure 3:
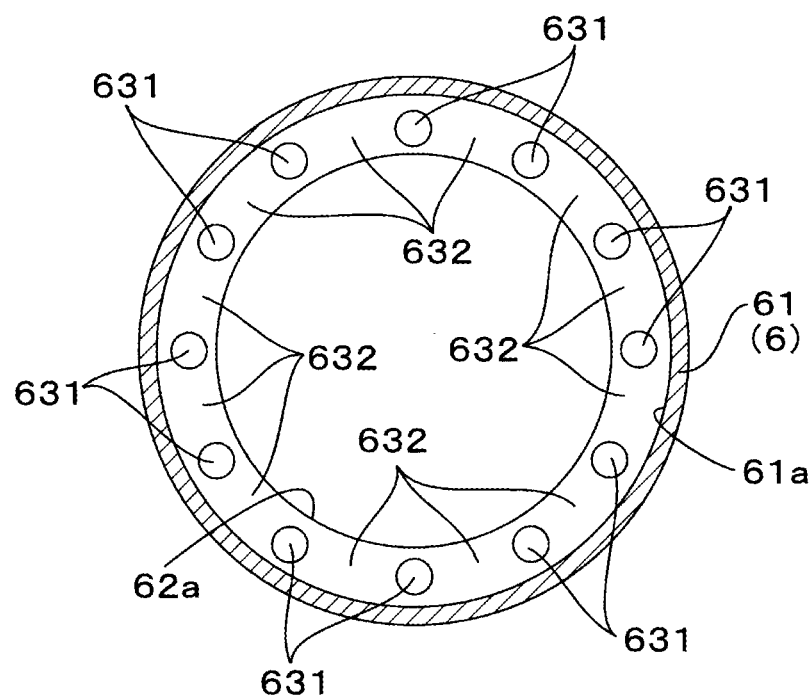
FIG. 3 is a sectional view of an atmospheric side cover, as taken along the line III-III in FIG. 1.

In this embodiment, the atmospheric side cover 6 is of a substantially cylindrical shape. The outer shoulder portion 63 is formed over an entire circumference of a middle portion of the atmospheric side cover 6 in the axial direction Y. The atmospheric side cover 6 has portions, as illustrated in FIG. 2, which form the outer shoulder portion 63 and protrude toward the front end side Y2 in the axial direction Y to form the contact portions 631 which contact the disc spring 7 serving as the biasing member. In this embodiment, the contact portions 631 are of a semi-circular shape and have tops 631a on the front end side Y2 which are placed in contact with the disc spring 7. In this embodiment, the twelve contact portions 631 are, as can be seen in FIG. 3, arranged at equal intervals away from each other in the circumferential direction of the atmospheric side cover 6. The detached portion 632 is formed between every adjacent two of the contact portions 631 and separate from the disc spring 7 (see FIG. 2) serving as the biasing member. A space between the detached portions 632 and the disc spring 7, as illustrated in FIG. 2, defines the communication path 52.

The inner diameter of the large-diameter portion 61 of the atmospheric side cover 6 is, as can be seen in FIG. 1, greater than the outer diameter of the atmospheric side insulator porcelain 32. The outer space 50 is formed between the inner peripheral surface 61a of the large-diameter portion 61 and the outer peripheral surface 32b of the atmospheric side insulator porcelain 32. The outer space 50 is located adjacent the seal 5 and communicates with the communication path 52.

The inner diameter of the small-diameter portion 62 of the atmospheric side cover 6 is, as illustrated in FIG. 1, slightly smaller than that of the large-diameter portion 61. The electrically conductive leads 14 are disposed inside the small-diameter portion 62 and connected to the end portion 21 of the sensor device 2 on the base end side Y1. The outside path 51 is formed inside the small-diameter portion 62 in communication with the communication path 52.

The base end portion 64 of the atmospheric side cover 6 opens to form the air hole 641. The filter cover 8 is mounted on the base end side Y1 of the atmospheric side cover 6. The filter cover 8 is substantially cylindrical and has the front end side Y2 in which a base end portion of the atmospheric side cover 6 is fit. The air pass portions 66 are formed in a side wall of the filter cover 8 over the circumference of the air hole 641 of the atmospheric side cover 6. The air pass portions 66 have the air filters 65 installed therein. The air is introduced into the atmospheric side cover 6 through the air pass portions 66. The air filters 65 serve to block entrance of water through the air pass portions 66. The air hole 641 (the air pass portions 66) communicates with the outside path 51, so that the outer space 50, the communication path 52, the outside path 51, and the air pass portions 66 communicate with each other.

Figure 4:
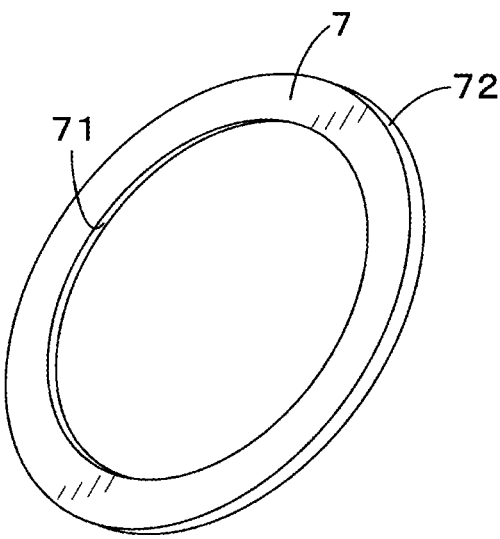
FIG. 4 is a perspective view of a biasing member in an embodiment 1.

The device-side insulator porcelain 31, as illustrated in FIG. 1, which retains the sensor device 2 therein and the atmospheric side insulator porcelain 32 which is disposed on the base end side Y1 of the device-side insulator porcelain 31 are provided. The disc spring 7 is arranged on the base end surface 32a of the atmospheric side insulator porcelain 32 as the biasing member. The disc spring 7 is placed so as to urge the atmospheric side insulator porcelain 32 against the device-side insulator porcelain 31 between the contact portions 631 and the atmospheric side insulator porcelain 32, thereby achieving adhesion between the front end surface 32c on the front end side Y2 of the atmospheric side insulator porcelain 32 and the base end surface 31a on the base end side Y1 of the device-side insulator porcelain 31 to create an air-tight seal therebetween. The disc spring 7, as illustrated in FIGS. 1 and 4, is an annular elastic member along the outer shoulder portion 63 and has the inner circumferential surface 51 and the outer circumferential surface 72 which are circular in a planar view. The outer diameter of the disc spring 7 is greater than the inner diameter of the small-diameter portion 62 of the atmospheric side cover 6 and slightly smaller than the inner diameter of the large-diameter portion 61.

The gas sensor 1, as illustrated in FIG. 1, has the measurement gas side cover 10 mounted on the front end side Y2 of the housing 4. The measurement gas side cover 10 includes the outer cover 11 and the inner cover 12. The outer cover 11 and the inner cover 12 each have a plurality of measurement gas inlets 13 through which the measurement gas is introduced to create the measurement gas atmosphere 100 within the measurement gas side cover 10.

The seal 5, as illustrated in FIG. 1, includes the metallic ring 54 which is swaged by the swaging portion 42 formed by a base end portion of the housing 4, the insulating member 55 which electrically isolate between the sensor device 2 and the housing 4, and the power sealing member 56 which is made of talc. The seal 5 hermetically isolates between the measurement gas atmosphere 100 formed on the front end side Y2 of the gas sensor 1 and the air atmosphere 30 formed on the base end side Y1 of the gas sensor 1.

The gas sensor 1 of this embodiment may experience deformation of the seal 5 due to high-temperature or high-pressure in the internal combustion engine. The deformation of the seal 5 results in leakage of the measurement gas G from the seal 5. In the gas sensor 1, the measurement gas G leaking from the seal 5, as illustrated in FIG. 1, reaches the outer space 50, flows into the outside path 51 through the communication path 52 formed in the outer shoulder portion 63, and is then discharged from the air hole 641 (i.e., the air pass portions 66) outside the atmospheric side cover 6. The outer shoulder portion 63 of the atmospheric side cover 6 presses the atmospheric side insulator porcelain 32 against the device-side insulator porcelain 31 through the disc spring 7 to ensure the air-tight seal therebetween. This avoids entry of the measurement gas G into the air atmosphere 30 formed as a reference gas within the atmospheric side cover 6, thereby ensuring a correct sensor output. The detached portion 632 and the contact portions 631 which define the communication path 52 are provided by the outer shoulder portion 63 of the atmospheric side cover 6, thereby alleviating concentration of stress on the base end surface 32a of the atmospheric side insulator porcelain 32 as compared with when the base end surface 32a of the atmospheric side insulator porcelain 32 is shaped to have irregularities, which avoids breakage of the atmospheric side insulator porcelain 32. The detached portion 632 and the contact portions 631 of the outer shoulder portion 63 of the atmospheric side cover 6 may be made easily using a press, thus resulting in a decrease in manufacturing cost as compared with when the base end surface 32a of the atmospheric side insulator porcelain 32 is shaped to have irregularities to define a path between itself and the outer shoulder portion 63 of the atmospheric side cover 6.

The communication path 52 is formed on the outer shoulder portion 63 of the atmospheric side cover 6, so that it is located close to the outside air, thereby facilitating dissipation of heat therefrom, so that it is kept at a relatively low temperature as compared with when the atmospheric side insulator porcelain 32 is shaped to have irregularities to define a flow path between itself and the outer shoulder portion 63. Such thermophoresis causes the measurement gas G leaking from the seal 5 to actively flow in the communication path 52 that is lower in temperature, not inside the atmospheric side insulator porcelain 32 that is higher in temperature, thereby avoiding the entry of the measurement gas G escaping from the seal 5 into the air atmosphere 30 in the atmospheric side insulator porcelain 32 to ensure a correct sensor output.

Figure 5:
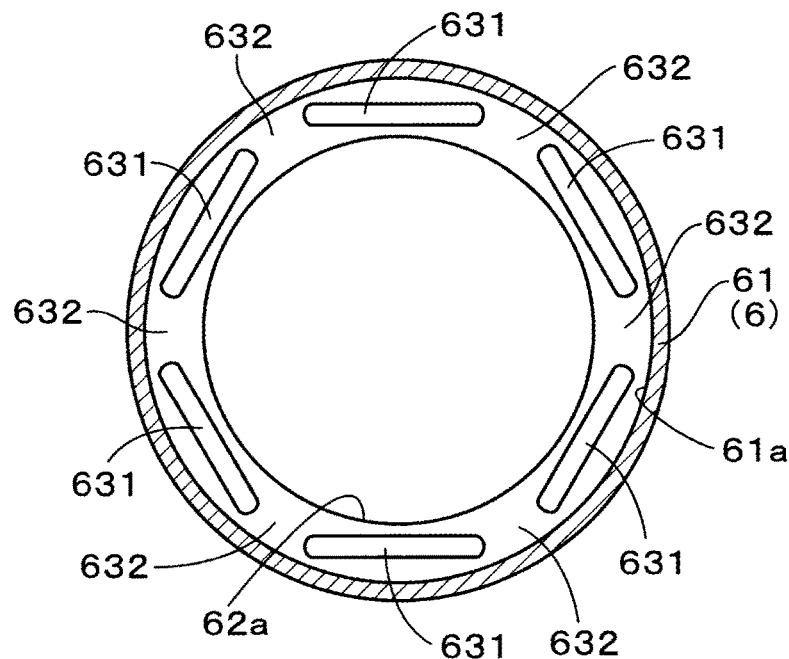
FIG. 5 is a sectional view of an atmospheric side cover in the first modified form of an embodiment 1, as taken along the line III-III in FIG. 1.
Figure 6:
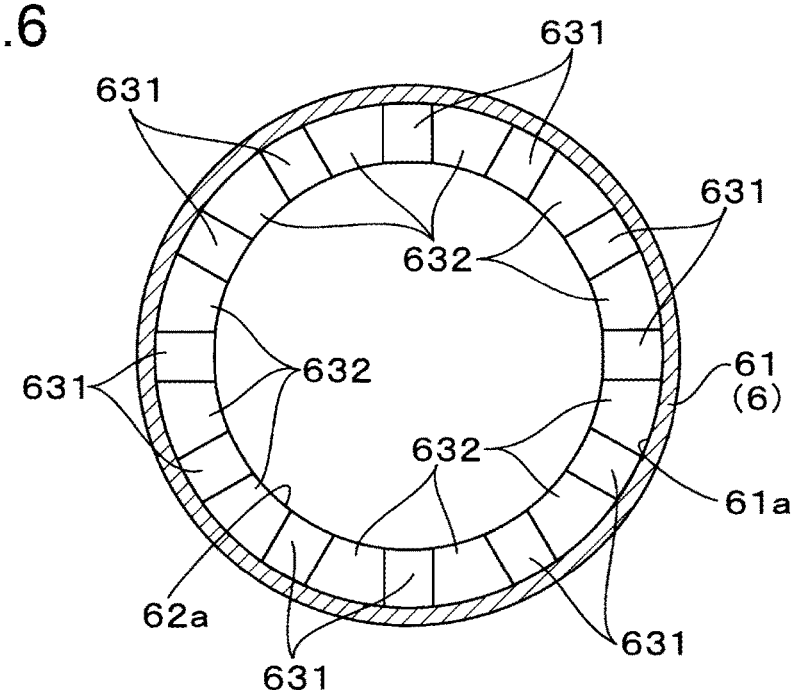
FIG. 6 is a sectional view of an atmospheric side cover in the second modified form of an embodiment 1, as taken along the line III-III in FIG. 1.
Figure 7:
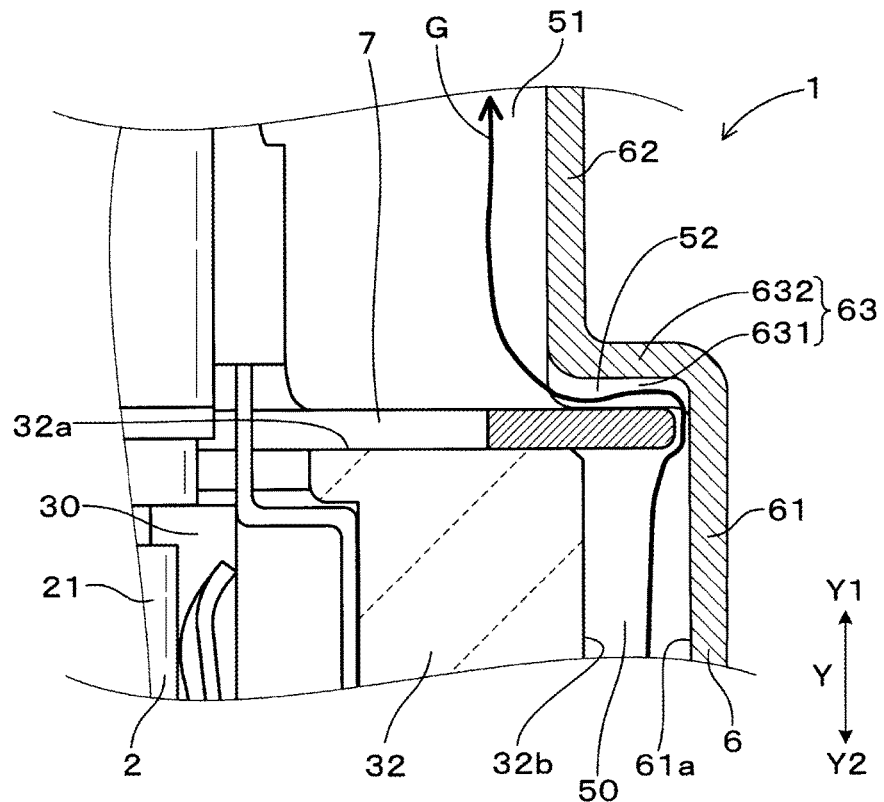
FIG. 7 is an enlarged view around a region of a shoulder portion in the second modified form of an embodiment 1.

The contact portions 631 are formed to protrude in the form of a half-sphere on the front end side Y2 of the outer shoulder portion 63 to define the detached portion 632 between the adjacent contact portions 631, but may alternatively be, as illustrated in FIG. 5, shaped in the form of a rib to protrude from the front end side Y2 of the outer shoulder portion 63 and extend in a direction of a tangent line to the inner peripheral surface 62a of the small-diameter portion 62 to form the detached portion 632 between every adjacent two of the contact portions 631. The contact portions 631 may alternatively be, as illustrated in FIGS. 6 and 7, formed in the form of a rib to protrude from the base end side Y1 of the outer shoulder portion 63 and extend radially to form the detached portion 632 between every adjacent two of the contact portions 631. Either case offers the same beneficial advantages as in the above embodiment.

As apparent from the above discussion, this embodiment provides the gas sensor 1 which is designed to avoid the entry of the measurement gas into the air atmosphere 30 within the atmospheric side insulator porcelain 32, thereby obtaining a correct sensor output, eliminating a risk of breakage of the atmospheric side insulator porcelain 32, and decreasing the manufacturing costs thereof.

Embodiment 2

Figure 8:
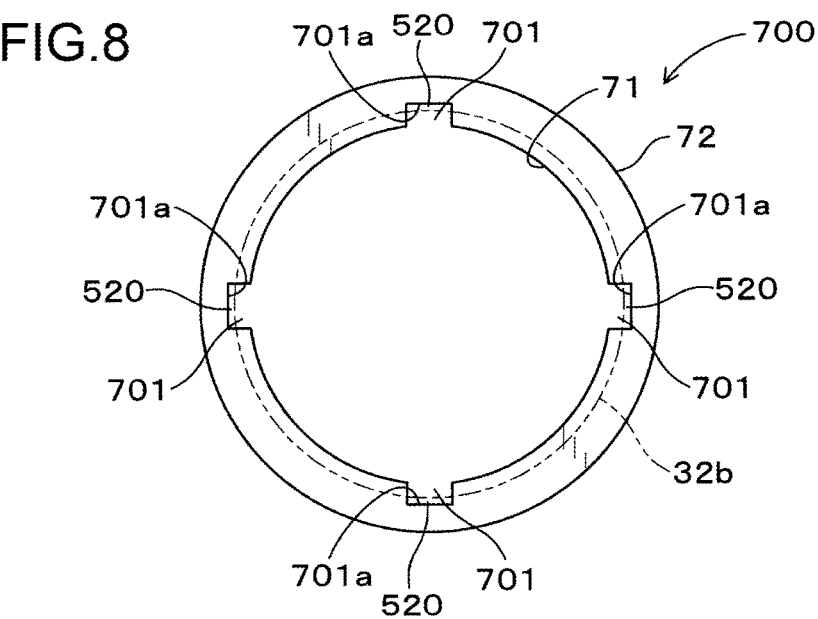
FIG. 8 is a top view of a biasing member in an embodiment 2.

The gas sensor 1 of this embodiment is equipped with the disc spring 700 illustrated in FIG. 8 as the biasing member instead of the disc spring 7 (see FIG. 3) installed in the gas sensor 1 of the first embodiment. The disc spring 700 is an annular elastic member along the outer shoulder portion 63 and has a plurality of cut-out portions 701 formed in the inner circumferential surface 71 to define gas drain portions 520 leading to the communication path 52. The four cut-out portions 701 are arranged in an interval of 90°. Each of the cut-out portions 701 is formed in a rectangular as viewed from the axial direction Y and has the radially outer surface 701a which is located outside the outer peripheral surface 32b of the atmospheric side insulator porcelain 32 in the radial direction. This, as can be seen in FIG. 8, defines the gas drain portions 520 between the cut-out portions 701 and the outer peripheral surface 32b of the atmospheric side insulator porcelain 32, as viewed from the axial direction Y. The gas drain portions 520 communicate with the communication path 52 (see FIG. 9). Other arrangements are identical with those in the first embodiment. The same reference numbers as employed in the first embodiment refer to the same parts, and explanation thereof in detail will be omitted here.

Figure 9:
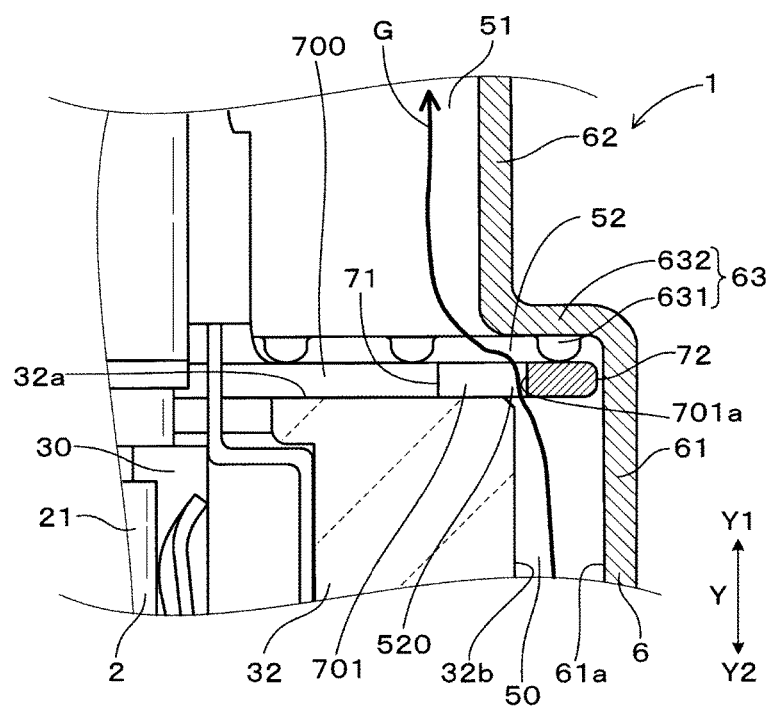
FIG. 9 is an enlarged view around a region of a shoulder portion of a gas sensor in an embodiment 2.

The measurement gas G leaking from the seal 5 (see FIG. 1) flows, as can be seen in FIG. 9, from the outer space 50 into the communication path 52 through the gas drain portions 520, reaches the outside path 51, and then is discharged from the air pass portions 66 (see FIG. 1). This causes the measurement gas G escaping from the seal 5 to flow in the communication path 52, thereby avoiding the entry of the measurement gas G into the air atmosphere 30 within the atmospheric side insulator porcelain 32 (see FIG. 1), and obtaining a correct sensor output. The same other beneficial advantages as in the first embodiment are offered.

Figure 10:
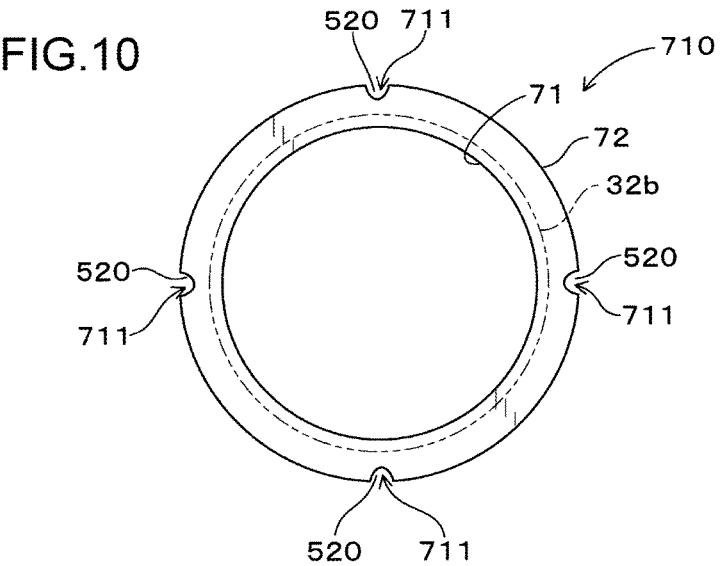
FIG. 10 is a top view of a biasing member in the first modified form of an embodiment 2.
Figure 11:
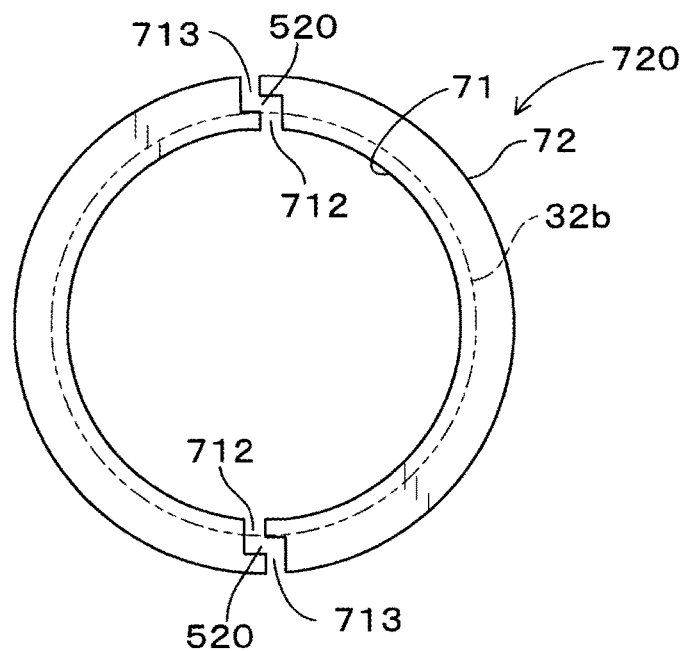
FIG. 11 is a top view of a biasing member in the second modified form of an embodiment 2.
Figure 12:
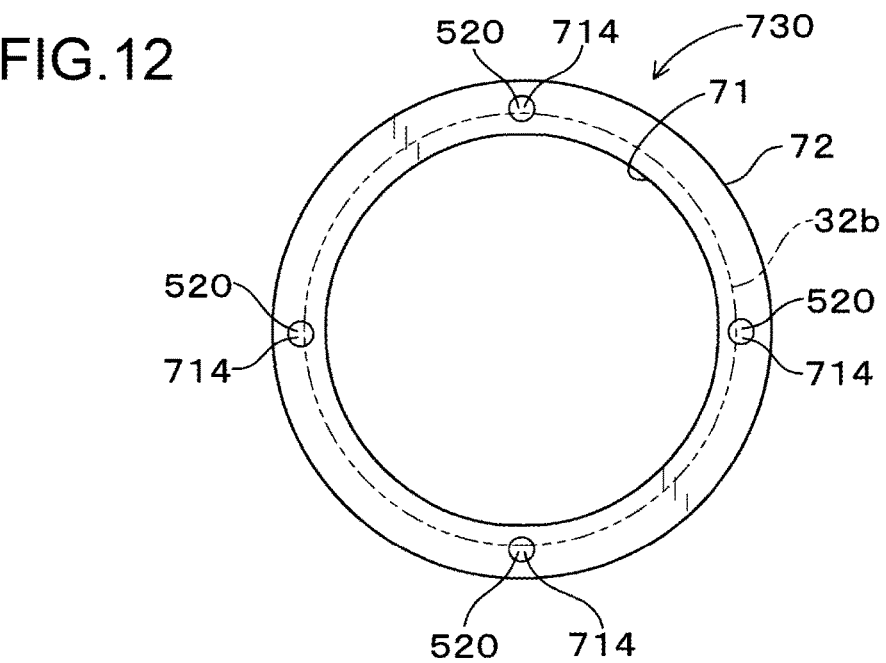
FIG. 12 is a top view of a biasing member in the third modified form of an embodiment 2.

The disc spring 700 has the cut-out portions 701 formed in the inner circumferential surface 71 to define the gas drain portions 520, but instead, a plurality of cut-out portions 711 may be, as illustrated in FIG. 10, formed in the outer circumferential surface 72 of the disc spring 710 to define the gas drain portions 520. For instance, the four cut-out portions 711 are located at equal intervals of 90°. Alternatively, the disc spring 720, as illustrated in FIG. 11, may have cut-out portions 712 and 713 formed in the outer circumferential surface 72 and the inner circumferential surface 71, respectively, to define the gas drain portions 520. In the example of FIG. 11, the two cut-out portions 712 and the two cut-out portions 713 are provided in the disc spring 720. The cut-out portions 712 communicate with the cut-out portions 713. The disc spring 720 is, therefore, made up of two separate parts to have gaps between the separate parts to define the gas drain portions 520. Alternatively, the disc spring 730, as illustrated in FIG. 12, may have through-holes 714 formed therein to define the gas drain portions 520.

Embodiment 3

Figure 13:
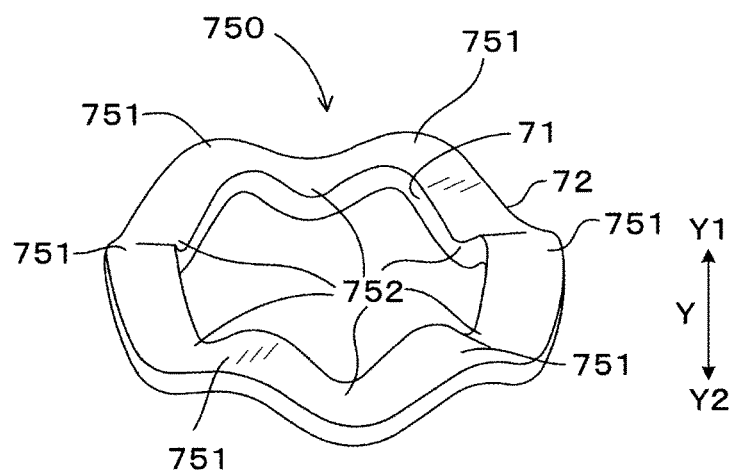
FIG. 13 is a perspective view of a biasing member in an embodiment 3.
Figure 14:
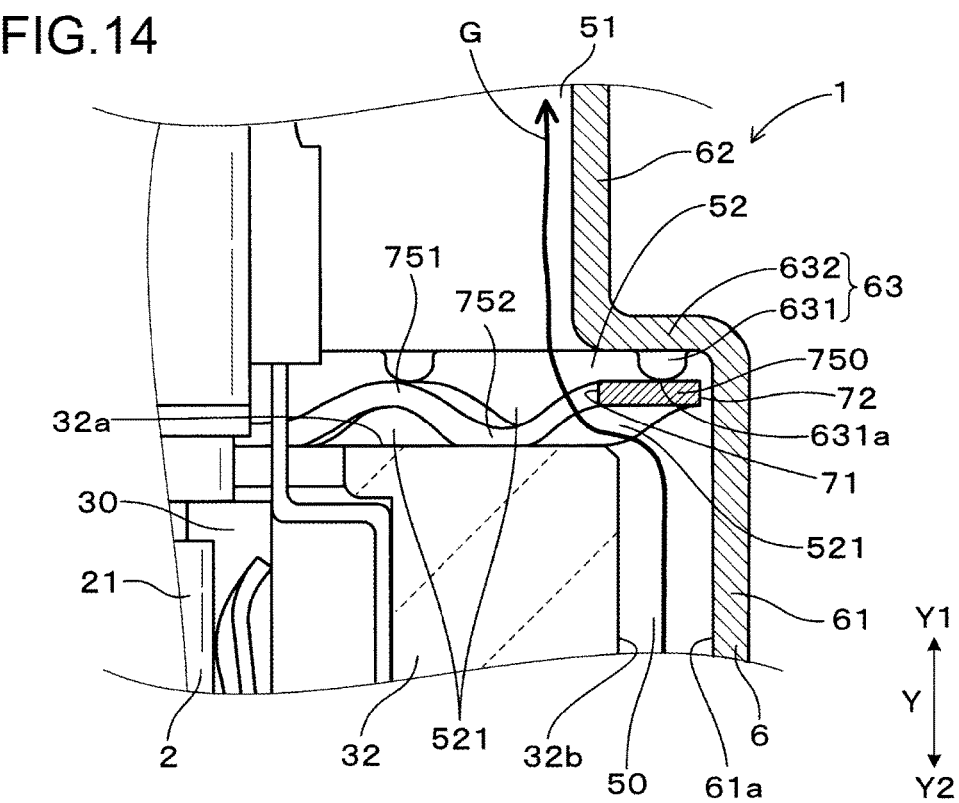
FIG. 14 is an enlarged sectional view around a region of a shoulder portion of a gas sensor of an embodiment 3.

The gas sensor 1 of this embodiment is, as illustrated in FIG. 13, equipped with the wave washer 750 as the biasing member instead of the disc spring 3 (see FIG. 3) of the gas sensor 1 of the first embodiment. The wave washer 750 is, as be seen in FIGS. 13 and 14, an annular elastic member along the outer shoulder portion 63 and includes base end side curved portions 751 protruding to the base end side Y1 and front end side curved portions 752 protruding to the front end side Y2. The gas drain portions 521 which lead to the communication path 52 are, as illustrated in FIG. 14, formed between the base end side curved portions 751 and the atmospheric side insulator porcelain 32 and between the front end side curved portions 752 and the outer shoulder portion 63. Other arrangements are identical with those in the first embodiment. The same reference numbers as employed in the first embodiment refer to the same parts, and explanation thereof in detail will be omitted here.

The measurement gas G leaking from the seal 5 (see FIG. 1) flows, as can be seen in FIG. 14, from the outer space 50 into the outside path 51 through the communication path 52 and the gas drain portions 521 and then is discharged from the air pass portions 66, thereby obtaining, like in the embodiment 2, a correct sensor output.

Embodiment 4

Figure 15:
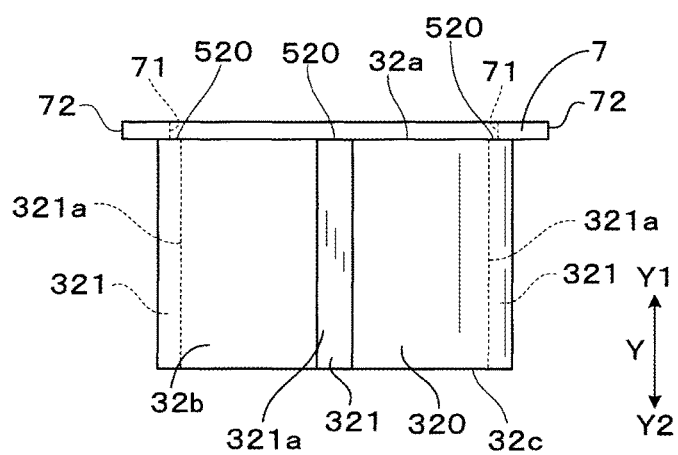
FIG. 15 is a side view of a biasing member and an atmospheric side insulator porcelain in an embodiment 4.
Figure 16:
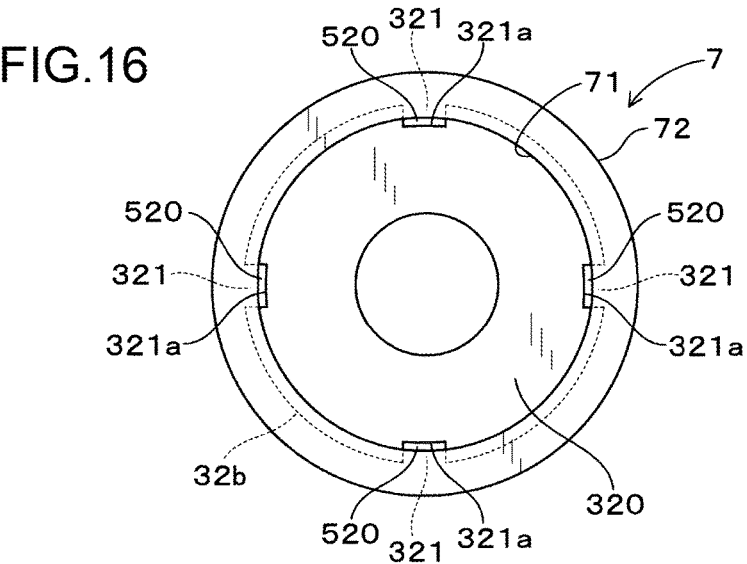
FIG. 16 is a top view of a biasing member and an atmospheric side insulator porcelain in an embodiment 4.
Figure 17:
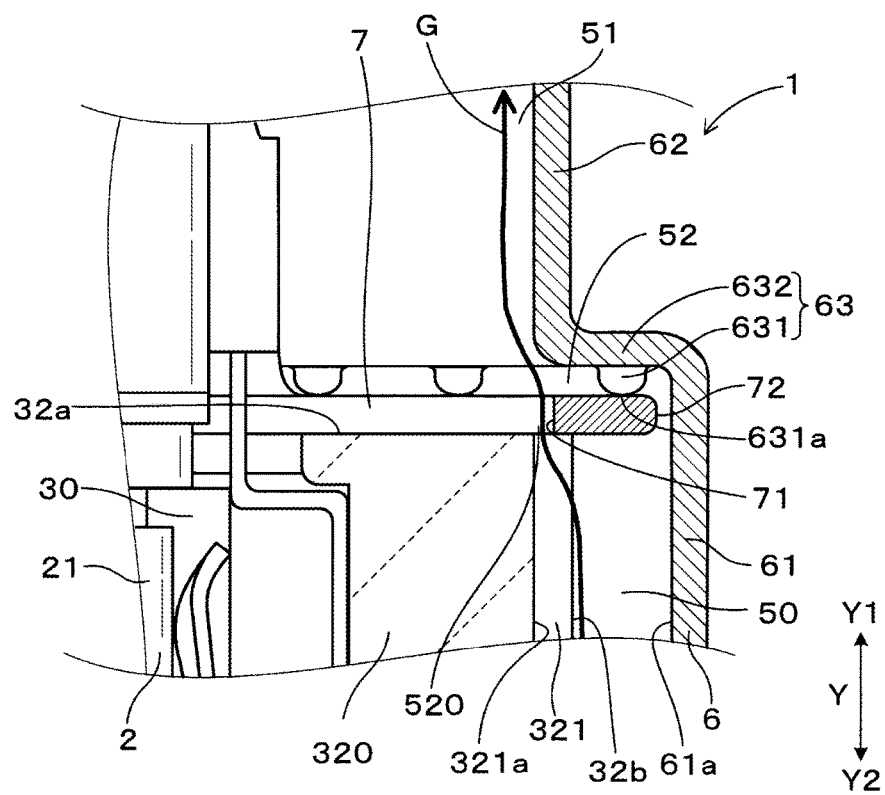
FIG. 17 is an enlarged sectional view around a region of a shoulder of a gas sensor in an embodiment 4.

The gas sensor 1 of this embodiment is, as illustrated in FIGS. 15 to 17, equipped with the atmospheric side insulator porcelain 320 instead of the atmospheric side insulator porcelain 32 (see FIG. 1) of the first embodiment. The atmospheric side insulator porcelain 320 has grooves 321 formed in the outer peripheral surface 32b. The grooves 321 extend in the axial direction Y and lead to the communication path 52. The grooves 321 has the radially inside surface 321a located inside the inner circumferential surface 71 of the disc spring 7 in the radial direction, as viewed from the axial direction Y, thereby defining the gas drain portions 520, as can be seen in the axial direction Y in FIG. 16, between the inner circumferential surface 71 of the disc spring 7 and the grooves 321 of the atmospheric side insulator porcelain 320. Other arrangements are identical with those in the first embodiment. The same reference numbers as employed in the first embodiment refer to the same parts, and explanation thereof in detail will be omitted here.

The measurement gas G leaking from the seal 5 (see FIG. 1) flows, as can be seen in FIG. 17, from the outer space 50 into the outside path 51 through the gas drain portions 520 and the communication path 52 and then is discharged from the air pass portions 66. This causes the measurement gas G escaping from the seal 5 to flow in the communication path 52, thereby avoiding the entry of the measurement gas G into the air atmosphere 30 within the atmospheric side insulator porcelain 320 (see FIG. 1), and obtaining a correct sensor output. The same other beneficial advantages as in the first embodiment are offered.

Like the embodiment 2, the disc spring 700 may be provided as the biasing member. In this case, the cut-out portions 701 (see FIG. 8) formed in the disc spring 700 may overlap the grooves 321, as viewed in the axial direction Y or be placed in misalignment therewith. In either case, the beneficial effects, as provided by the cut-out portions 701 in the embodiment 2, are added to those in the embodiment 4, thereby obtaining a more correct sensor output.

Figure 18:
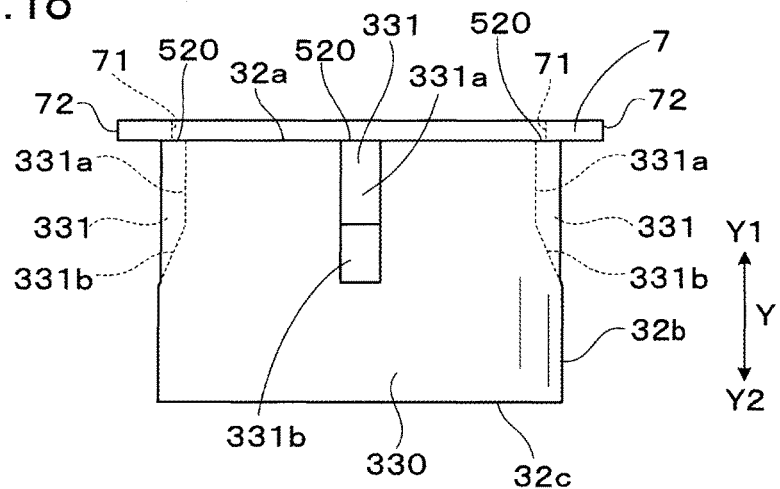
FIG. 18 is a side view of a biasing member and an atmospheric side insulator porcelain in the first modified form of an embodiment 4.

The outer peripheral grooves 321 are, as illustrated in FIG. 17, formed to continuously extend from the end of the outer peripheral surface 32b of the atmospheric side insulator porcelain 320 on the base end side Y1 to the end of the outer peripheral surface 32b on the front end side Y2, but instead, the outer peripheral grooves 331, as illustrated in FIG. 18, may be formed in the outer peripheral surface 32b of the atmospheric side insulator porcelain 330 so as to extend from the base end surface 32a on the base end side Y1 of the atmospheric side insulator porcelain 330 to a middle portion of the outer peripheral surface 32b in the axial direction Y. Of the radially inside surfaces 331a and 331b of the outer peripheral grooves 331, the radially inside surfaces 331a on the base end side Y1 extend parallel to the axial direction Y, while the radially inside surfaces 331b on the front end side Y2 are inclined radially outwardly relative to the axial direction Y as approaching the front end side Y2. This structure offers substantially the same beneficial advantages as those in the embodiment 4.

Figure 19:
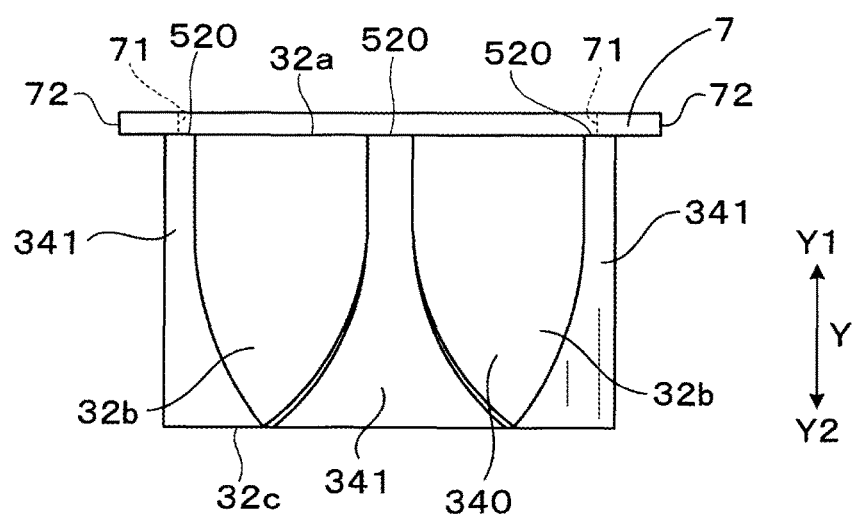
FIG. 19 is a side view of a biasing member and an atmospheric side insulator porcelain in the second modified form of an embodiment 4.

Instead of the outer peripheral grooves 321 in FIG. 17, the atmospheric side insulator porcelain 340 may have, as illustrated in FIG. 19, outer peripheral grooves 341 formed in the outer peripheral surface 32b. The outer peripheral grooves 341 extend in the axial direction Y and spread in the circumferential direction as approaching to the front end side Y2. In this case, the outer peripheral grooves 341 serve to direct the measurement gas G escaping from the seal 5 (see FIG. 1) to the gas drain portions 520 along the configuration of the outer peripheral grooves 341, so that the measurement gas G is actively discharged to the outside through the communication path 52 and the outside path 51 (see FIG. 1), thereby avoiding the entry of the measurement gas G into the air atmosphere 30 of the atmospheric side insulator porcelain 340 (see FIG. 1) and obtaining a more accurate sensor output.

EXPLANATION OF REFERENCE SYMBOL 1 gas sensor
2 sensor device
31 device-side insulator porcelain
32, 320, 330, 340 atmospheric side insulator porcelain
4 housing
5 seal
50 outer space
51 outside path
52 communication path
520, 521 gas drain portion
6 atmospheric side cover
61 large-diameter portion
62 small-diameter portion
63 outer shoulder
7, 700, 710, 720, 730 disc spring (biasing member)
750 wave washer (biasing member)

The invention claimed is:
1. A gas sensor comprising: a sensor device which detects a concentration of a given gas component of measurement gas; a device-side insulator porcelain which retains the sensor device therein; an atmospheric side insulator porcelain which covers a base end side of the sensor device to define an air atmosphere; a housing which retains said the device-side insulator porcelain and said atmospheric side insulator porcelain therein; a seal which is made of a sealing member disposed between an inner peripheral surface of the housing and an outer peripheral surface of the device-side insulator porcelain; and an atmospheric side cover which is secured to a base end side of said housing,
wherein said atmospheric side cover includes a large-diameter portion which is formed on a front end side thereof, a small-diameter portion which is formed closer to the base end side than the large-diameter portion is and has a diameter smaller than that of the large-diameter portion, a shoulder portion which is formed between the small-diameter portion and the large-diameter portion to press a base end surface of the atmospheric side insulator porcelain to the front end side through a biasing member to place the atmospheric side insulator porcelain in contact with the device-side insulator porcelain, and an air hole which is formed in a base end portion, wherein an outer space is formed between an outer peripheral surface of the atmospheric side insulator porcelain and an inner peripheral surface of the large-diameter portion, the outer space being arranged adjacent to the seal, wherein an outside path is formed inside the small-diameter portion in communication with the air hole, and wherein the shoulder portion includes a contact portion which contacts the biasing member and a detached portion which is separate from the biasing member, a communication path being formed between the detached portion and the biasing member to establish communication between the outer space and the outside path.

2. A gas sensor as set forth in claim 1, wherein the biasing member is an annular elastic member along the shoulder portion and has formed therein a cut-out portion to define a gas drain portion easing to said communication path.

3. A gas sensor as set forth in claim 1, wherein said biasing member is an annular elastic member along the shoulder portion and includes a base end side curved portion protruding to the base end side and a front end side curved portions protruding to the front end side, and wherein gas drain portions are formed between the base end side curved portion and the atmospheric side insulator porcelain and between the front end side curved portion and the shoulder portion, the gas drain portions leading to the communication path.

4. A gas sensor as set forth in claim 1, wherein the atmospheric side insulator porcelain has an outer peripheral groove formed in the outer peripheral surface, the outer peripheral groove extending in an axial direction and communicating with the communication path.

* * * * *